US006368581B1

(12) United States Patent
Karlen et al.

(10) Patent No.: US 6,368,581 B1
(45) Date of Patent: Apr. 9, 2002

(54) HAIR STYLING OIL

(75) Inventors: Thomas Karlen, Basel (CH); Axel Kalbfleisch, Darmstadt (DE); Michael Franzke, Rossdorf (DE); Chantal Borcard, La Joux (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/577,535

(22) Filed: May 24, 2000

(30) Foreign Application Priority Data

May 28, 1999 (DE) .......................... 199 24 705

(51) Int. Cl.$^7$ ................................ A61K 7/06
(52) U.S. Cl. ................. 424/70.1; 424/70.11; 424/70.19
(58) Field of Search ............................. 424/70.2, 70.31, 424/70.1, 70.11, 70.19

(56) References Cited

U.S. PATENT DOCUMENTS 6,156,298 A * 12/2000 Karlen et al. ............ 424/70.31

FOREIGN PATENT DOCUMENTS

EP 0 312 995 A2 4/1989
EP 0 445 659 A2 9/1991
EP 0445659 A2 * 11/1991 ............ A61K/7/11

OTHER PUBLICATIONS

Harry's Cosmeeticology, Seventh Edition, Edited by J. B. Wilkinson and R.J. Moore, Chemical Publishing New York, Chapter Hair Setting Lotions, Aprays and Dresings, pp. 470–471, 482–485.

* cited by examiner

Primary Examiner—Thurman K. Page
Assistant Examiner—Robert M. Joynes
(74) Attorney, Agent, or Firm—Michael J. Striker

(57) ABSTRACT

The hair treatment composition has the Theological properties of an oil but contains non-hydrophobic ingredients. It includes at least one fatty acid glyceride polyalkylene glycol ether or at least one fatty acid partial glyceride polyalkylene glycol ether with at least 30 alkylene glycol units respectively; at least one surfactant different from the at least one fatty acid glyceride polyalkylene glycol ether and the at least one fatty acid partial glyceride polyalkylene glycol ether with at least 30 alkylene glycol units and at least one thickener. The hair treatment composition is dfree of ingredients that cause foaming of the composition prior to or during application to hair. It provides hair to which it is applied with improved hair shaping, long-lasting luster and soft feel. It behaves like an oil, without having an oil in the classical sense as its principal ingredient.

14 Claims, No Drawings

HAIR STYLING OIL

BACKGROUND OF THE INVENTION

1. Field of the Invention

The subject matter of the present invention is a hair treatment agent, which has the consistency of a hair oil without containing hydrophobic ingredients and which contains a fatty acid glyceride polyalkylene glycol ether with at least 30 alkylene glycol units or a fatty acid partial glyceride polyalkylene glycol ether with at least 30 alkylene glycol units, an additional nonionic surfactant and a thickener.

2. Prior Art

Research has been performed for a longtime in the field of hair treatment compositions in the form of oils, which make styling easier and increase the luster and hold of the hairstyle. Normally hydrophobic oils in the usual sense, i.e. natural, animal or vegetable oils, mineral oils, higher hydrocarbon substances (e.g. paraffins), synthetic oils or silicone oils, have been used to obtain the desired shaping and luster-producing properties. The problem with this type of oil is the high hair loading and the poor washability of these hydrophobic substances. The problem of stabilizing the formulation arises with aqueous preparations, which tend to separate into aqueous and lipophilic phases.

It is also possible to use nonionic surfactants, such as fatty alcohol ethoxylates and fatty acid ethoxylates, such as luster and shaping agents. The nonionic surfactants do not facilitate improved hair feel and hair luster, which the user expects from hair oils. The use of high proportions of non-aqueous solvents, such as higher alcohols, glycerol or polyethylene glycols of course improves the luster, but impairs the shaping of the treated hair.

SUMMARY OF THE INVENTION

It is thus an object of the present invention to provide a hair treatment composition with the consistency and positive application properties of a hair oil, which however does not have negative properties that produce a high content of hydrophobic substances. Especially the composition should increase the stylability, the control and the luster of the hair and be easy to handle, and satisfactorily worked into the hair and again washable from the hair.

This object is attained by using a special highly ethoxylated nonionic surfactant, which already leads in small amounts to a composition, which has the expected action of an oil, but may be easily worked into the hair and imparts good stylability and long-lasting luster to the hairstyle as well as providing a soft feel to the hair. Surprisingly it has been found that the composition according to the invention has the expected characteristics of an oil, although its principal ingredient is not an oil and the composition is again easily washed from the air without leaving a residue.

The hair treatment composition of the invention with the Theological properties of an oil thus includes non-hydrophobic ingredients and comprises:

(A) at least one fatty acid glyceride polyalkylene glycol ether or a fatty acid partial glyceride polyalkylene glycol ether with at least 30 alkylene glycol units;

(B) at least one additional surfactant different from the surfactants of (A); and (C) at least one thickener, and the composition is free of ingredients, which cause foaming of the composition prior to or during use. The partial glycerides can be mono- or diglycerides or a mixture of mono- and diglycerides. Non-hydrophobic ingredients in the sense of this application especially are hydrophilic and amphiphilic ingredients. The hair treatment composition according to the invention contains anionic, cationic or amphoteric surfactants at must up to an amount below which no foaming occurs when the composition is worked into the hair and which is free of propellants or mechanical devices, which cause foaming of the product during application.

The subject matter of the invention also includes a method of using a fatty acid glyceride polyalkylene glycol ether or a fatty acid partial glyceride polyalkylene glycol ether with 30 to 1000 alkylene glycol units to make a hair treatment composition with the rheological properties of an oil.

The term "rheological properties" of an oil in the sense of the present invention means the consistency, which is more viscous than water but in contrast to a gel free-flowing and without a permanent shape, i.e. flows off an inclined surface at a temperature of about 25° C. The viscosity amounts to preferably from 200 to 4000 m²/s at 25° C., especially preferably from 1000 to less than 4000 at 25° C. measured with a Haake VT-550 rotation viscometer and a Schergradient of 100 s⁻⁵.

The composition according to the invention contains ingredient (A) preferably in an amount of from 0.1 to 30 percent by weight, especially preferably from 0.3 to 20 or 0.5 to 12 percent by weight. Ingredient (A) is selected from compounds of the formula (I):

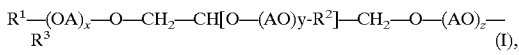

$$R^1\text{—(OA)}_x\text{—O—CH}_2\text{—CH[O—(AO)y-R}^2\text{]—CH}_2\text{—O—(AO)}_z\text{—}\\R^3 \quad (I),$$

wherein $R^1$, $R^2$ and $R^3$ are each, independently of each other, hydrogen or a saturated or unsaturated, branched or non-branched $C_6$- to $C_{22}$-acyl groups, which, if necessary, can be substituted with one or more hydroxy group, wherein at least one of the substituents $R^1$, $R^2$ and $R^3$ is one of the saturated or unsaturated, branched or non-branched $C_6$- to $C_{22}$-acyl groups; A is an alkylene group with two or three carbon atoms; x, y and z are numbers between 0 and 1000, and the sum x+y+z is from 30 to 1000, preferably from 30 to 500, especially preferably from 70 to 250. Compounds are especially preferred in which $R^1$ is hydrogen, $R^2$ is selected from the group consisting of H and a $C_6$- to $C_{22}$-acyl group and $R^3$ is $C_6$- to $C_{22}$-acyl group, A is an ethylene group and x and y equal 0.

Examples of compounds that are suitable as ingredient (A) include polyethylene glycol (30)-glyceryl cocoate, polyethylene glycol (80)-glyceryl cocoate, polyethylene glycol (80)-glyceryl tallowate, polyethylene glycol (120)-glyceryl stearate, polyethylene glycol (200)-glyceryl stearate, polyethylene glycol (200)glyceryl tallowate, hydrogenated polyethylene glycol (200)-glyceryl palmitate. Polyethylene glycol (200)-glyceryl palmitate is especially preferred.

Ingredient (B) of the composition of the invention is at least one additional, preferably nonionic, surfactant in an amount of preferably from 0. 1 to 30 percent by weight, especially preferably from 0.5 to 20 percent by weight. The kind and amount of the surfactants are selected so that the composition according to the invention does not produce a foam either when it is dispensed from its container or when it is applied and worked into the hair. A nonionic, anionic, cationic or amphoteric surfactant can be used, but the nonionic surfactants are especially preferred. Suitable nonionic surfactants include, e.g., ethoxylated fatty acids with 10 to 26 carbon atoms, ethoxylated fatty alcohols with 10 to 26 carbon atoms, alkoxylated fatty acid esters, ethoxylated hydrogenated or non-hydrogenated caster oil, glyceride alkoxylates, fatty acid glyceride polyalkylene glycol ether or fatty acid partial glyceride polyalkylene ether with less than 30 alkylene glycol units respectively, for example polyethylene glycol (7)-glyceryl cocoate, polyglycol amides, ethoxylated or non-ethoxylated fatty acid polyol esters and alkyl polyglycosides. The degree of ethoxylation of the ethoxylated surfactants is preferably greater than 3.

Examples of suitable fatty alcohol ethoxylates include ethoxylated lauryl-, tetradecyl-, cetyl-, oleyl- or stearyl alcohol, which can be used alone or in mixtures with each other, or ethoxylated lanolin. Suitable ethoxylated fatty acids include for example polyethylene glycol (75)-laurate, polyethylene glycol(90)-stearate, polyethylene glycol(120)-stearate, polyethylene glycol(120)-propylene glycol stearate, polyethylene glycol(150)-dilaurate or polyethylene glycol(175)-distearate.

Suitable polyesters include, e.g., ethoxylated and non-ethoxylated sugar esters, sorbitol esters and glycerol esters. Ethoxylated sorbitan fatty acid esters with the INCI-name polysorbate, non-ethoxylated sorbitan esters, such as sorbitan laurate, sorbitan palmitate, etc., non-ethoxylated glycerol esters, such as glyceryl stearate and glucose derivatives, such as polyethylene glycol(120)-methyl glucose dioleate and alkyl polyglucosides, such as, e.g., coco-glucosides, lauryl glucosides or decyl glucosides, are examples of these polyesters.

The thickener ingredient (C) is contained in an amount such that the entire composition has the rheological properties of an oil. The preferred compositions have a viscosity of from 200 to 4000 mm$^2$/s at 25° C., especially preferably from 1000 to 4000 mm$^2$/s at 25° C., measured with a Haake VT-550 rotary viscometer at 25° C. and a shear rate of 100 s$^{-1}$. The exact amount used depends on the nature of the thickener. Typical thickener concentrations used are from 0.05 to 3 percent by weight, especially preferably from 0.1 to 1% by weight.

Natural or synthetic polymers with thickening action or inorganic thickeners are used as the thickener ingredient (C). Nonionic and anionic polymers are especially preferred. Examples of thickeners, which can be contained in the composition of the invention, include the homopolymers of acrylic acid, which are known under the INCI destination Carbomer, acrylic acid/acrylic amide copolymers, sclerotium gum or copolymers of acrylic acid or methacrylic acid. Examples of suitable copolymers include, for example, acrylic or methacrylic acid lacryl- or methacrylic acid polyethoxyalkyl ester copolymers (e.g. acrylates/Seareth-20 methacrylate copolymer), acryl- or methacrylic acid/polyethoxyalkylallyl ether copolymers (e.g. steareth-10 allyl ether/acrylates copoymer) or acryl- or metharylic acid/itaconic acid polyethoxyalkyl ester copolymers (e.g. acrylates/steareth-20 itaconate copolymer and acrylates/ceteth-20 itaconate copolymer).

Furthermore natural thickeners, such as cellulose or celluslose derivatives, tragacanth, guar gum or guar derivatives, karaya gum, carraghen, xanthane, starch or starch derivatives may be used. Cellulose derivatives include, e.g., ethoxylated celluloses, hydroxyethyl cellulose, hydroxymethyl cellulose and methyl cellulose. Guar derivatives are, for example, guar hydroxypropyltrimonium chloride or hydroxy- propyl guar. Inorganic thickeners are, for example, bentonite or hectoite. Hydroxyethyl cellulose and cross-linked polyacrylic acids or their mixtures are especially preferred as thickeners in the compositions of the invention.

Preferred embodiments of the composition according to the invention are substantially free of cationic thickeners, since these ingredients are only completely removed with difficulty because of their substantivity for the hair.

Preferred embodiments of the composition according to the invention are also substantially free of thickeners with emulsifying properties, since these ingredients in combination with nonionic surfactants according to the invention can lead to a synergistic increase in viscosity, so that the behavior of the composition no longer corresponds to that of an oil. Emulsifying thickening polymers include cross-linked polymers, which contain long hydrocarbon side chains, ethoxylated as needed.

The composition according to the invention preferably is an aqueous or nonaqueous solution. The viscosity of the solution is preferably less than 4000 mm$^2$/s at 20° C. The alcohols used in the composition of the invention are univalent lower alcohols suitable for cosmetic purposes having 1 to 4 carbon atoms, such as ethanol or isopropanol, but also the lower multivalent alcohols, such as propylene glycols or glycerol may be used. The solvent is present in the composition of the invention in an amount of from 0.01 to 50 percent by weight, preferably in an amount of from 2 to 30 percent by weight.

Water-insoluble solvents, such as unbranched or branched hydrocarbons, like pentane, hexane and isopentane, and cyclic hydrocarbons, such as cyclopentane and cyclohexane, and paraffins, or isododecane, and synthetic or natural hydrophobic oils preferably are not contained in the compositions of the invention or only in such amounts which do not negatively influence the washability properties.

In a preferred embodiment the hair treatment composition according to the invention also includes preferably from 0.01 to 10 percent by weight, especially preferably from 0.1 to 8 percent by weight, of at least one film-forming, hair-fixing polymer, as additional ingredient (D). The polymer can be of synthetic or natural origin and can be nonionic, anionic, catione or amphoteric in nature. The hair fixing polymers can be used individually or in a mixture.

The term "film-forming, hair-fixing polymer", means a polymer, which is in a position when used in amounts from 0.1 to 5% by weight in an aqueous, aqueousalcoholic or alcoholic solution to deposit a film on the hair and to fix the hair in this manner.

Suitable synthetic, nonionic, film-forming hair-fixing polymers include homo- or copolymers, which are built up from at least one nonionic monomer. Suitable nonionic monomers include, for example, acryl amides, methacryl amides, alkyland dialkylacrylamides, alkyl- and dialkylmethacrylamides, alkylacrylates, alkylmethacrylates, vinyl caprolactone, vinyl pyrrolidone, vinyl ester, vinyl alcohol, propylene glycol or ethylene glycol, wherein the alkyl groups of these monomers preferably have from one to seven carbon atoms, especially preferably from one to three carbon atoms. Suitable synthetic nonionic polymers include, for example, homopolymers of vinyl pyrrolidone and homopolymers of N-vinyl-formamide. Additional suitable synthetic film-forming nonionic hair-fixing polymers include, for example, the copolymerizates of vinyl pyrrolidone and vinyl acetate, terpolymers made from vinyl pyrrolidone, vinyl acetate and vinyl propionate, polyacrylamides, polyvinylalcohols, polyethylene glycols with a molecular weight of from 800 to 20,000 g/mol.

Suitable anionic hair-fixing polymers include synthetic homo- or copolymers with neutralizable monomer units containing acid groups, which are copolymerizable with comonomers, if necessary, which contain no acid groups. The acid groups may include sulfonic acid groups, phosphoric acid groups and carboxylic acid groups, of which carboxylic acid groups are particularly preferred. Monomers containing suitable acid groups include, for example, acrylic acid, methacrylic acid, crotonic acid, maleic acid or maleic acid anhydride, aldehydocarboxylic acids or ketocarboxylic acids. The comonomers not substituted with acid groups include, e.g., acryl amide, methacrylamides, alkyl and dialkylacrylamides, alkyl and dialkylmethacrylamides, alkylacrylates, alkylmethacrylates, vinylcaprolactone, vinylpyrrolidone, vinyl esters, vinyl alcohol, propylene glycol or ethylene glycol, amine-substituted vinyl monomers, such as dialkylaminoalkylacrylates, dialkylaminoalkylmethacrylates, monoalkyl- aminoalkylacrylates and monoalkylaminoalkylmethacrylates, in which the alkyl groups of these monomers preferably contain one to seven carbon atoms, especially preferably from one to three carbon atoms.

Suitable anionic polymers include homopolymers of acrylic acid or methacrylic acid that are uncross-linked or cross-linked with polyfunctional agents, copolymers of acrylic acid or methacrylic acid with monomers selected from the group consisting of acrylic acid or methacrylic acid esters, acryl amides, methacrylamides and vinylpyrrolidones, homopolymers of crotonic acid and copolymers of crotonic acid with monomers selected from the group consisting of vinyl esters, acrylic acid or methacrylic acid esters, acrylamides and methacrylamides. A suitable natural polymer is, for example, shellac.

Preferred polymers with acid groups include cross-linked or uncross-linked vinyl acetate/crotonic acid copolymers, terpolymers of vinyl acetate, crotonic acid and polyethylene oxide, vinylpyrrolidone/vinyl acetate copolymers, terpolymers of acrylic acid, alkyl acrylate and N-alkylacrylamide, especially acrylic acid/ethyl acrylate/N-t-butylacrylamide terpolymer, terpolymers of vinyl acetate, crotonate and vinyl alkanoate, especially vinyl acetate/crotonate/vinyl neodecanoate copolymers, and methyl vinyl ether/maleic acid anhydride copolymers and their monoesters.

Anionic polyurethanes are an additional class of suitable anionic polymers. Preferred polyurethanes are characterized in that they have (a) terminal acid groups, which, for example, are introduced by aminosulfonic acids or aminocarboxylic acids, (b) if needed additional free carboxylic acid groups, which are introduced by polymerizing in carboxylic acid diols, such as dimethylolpropanoic acid, as comonomers and (c) polyurethane sequences, which are formed from polyester diols and diisocynates, such as alkylene diisocyantes or isophorone diisocyanates. Luviset® PUR of BASF, Germany, is suitable, for example.

The anionic polymers in the composition according to the invention are partially or completely neutralized with a cosmetically compatible neutralizing agent. Organic or inorganic bases can be used as the neutralizing agent. For example, suitable bases include, especially, aminoalkanols, such as aminomethylpropanol (AMP), triethanolamines or monoethanolamines, however ammonia, NaOH, among others, are also suitable.

Suitable natural film-forming polymers, or derivatives made from them by chemical reaction, include, for example, chitosan, hydroxyalkylchitosan, hydroxyalkylchitin, polysaccharides or mixture of oligo-, mono- and disaccharides, Chinese gum rosin (colophony), cellulose derivatives, such as hydroxypropyl cellulose with a molecular weight of from 30,000 to 50,000 g/mol, or shellac in neutralized or unneutralized form.

Suitable cationic hair-fixing polymers are characterized by at least one type of monomer which contains cationic or cationizable groups, preferably primary, secondary, tertiary or quaternary nitrogen groups. Suitable ammonium-substituted vinyl monomers are, for example, trialkylmethacryloxyalkyl ammonium groups, trialkylacryloxyalkyl ammonium groups, dialkyldiallyammonium groups and quaternary vinyl ammonium monomer groups with cyclic, cationic nitrogen-containing groups, such as pyridinium, imidazolium or quaternary pyrrolidones, e.g. alkylvinylimidizolium which can be substituted on the heterocyclic ring with up to 3 $C_1$- to $C_{12}$-alkyl groups, alkylvinylpyridinium or alkylvinylpyrrolidone salts. Suitable amine-substituted vinyl monomers include, for example, dialkylaminoalkylacrylates, dialkylaminoalkylmethacrylates, monoalkylaminoalkylarylates and monoalkyl- aminoalkylmethacrylates, N-vinylimidzole, which can be substituted with up to 3 $C_1$ to $C_{12}$-alkyl groups on the ring. The alkyl groups of these monomers are preferably lower alkyl groups with from one to seven carbon atoms, especially one to three carbon atoms. The cationic or basic monomers can be copolymerized with nonionic or nonbasic comonomers.

Suitable cationic polymers include, for example, polyvinylpyrrolidone/dimethylaminoethylmethacrylate copolymers, terpolymers of vinyl pyrrolidone, dimethylaminoethylmethacrylates and vinylcaprolactam, vinyl pyrrolidone/methacrylaminodpropyltrimethylammonium chloride copolymers, copolymers of vinyl pyrrolidone with quaternarized vinyl pyrrolidone/dimethylaminoethylmethacrylate copolymer, copolymerizates of vinyl pyrrolidone with vinylimidazolium methochloride, polymers of dimethyldiallylammonium salts and their copolymers with esters or amides of acrylic or methacrylic acid, condensates made from polyglycols and polyamines, cationic derivatized silicones, e.g. diquaternary polydimethylsiloxanes, cationic derivatized protein hydrolyzates and quaternarized cellulose or guar derivatives.

Cationic polymers, which contain basic groups, can be completely or partially neutralized with organic or inorganic acids.

Suitable amphoteric polymers are those which contain both cationic or groups catonizable by protonation and also anionic or groups anionizable by deprotonation. Cationic groups are, for example, quaternary amino groups, cationizable groups are, for example, primary, secondary or tertiary amine groups. Anionic groups include, for example, carboxylate, sulfate, phosphate or phosphonate groups. Anionizable groups include, for example, the protonated forms of the named anionic groups.

Suitable amphoteric polymers are, for example, copolymers made from octylacrylamide, t-butylaminoethylmethacrylate and two or more monomers, comprising acrylic acid, methacrylic acid or their esters. At least one type of monomer contains an acid group. Further examples include copolymers of acrylic acid, methacrylate and methacrylamideopropyltrimethylammonium chloride (INCI: polyquaternium-47), copolymers made from acrylamidopropyltrimonium chloride and acrylates or copolymers made from acrylamide, acrylamidopropyltrimonium chloride, 2-amidopropylacrylamide sulfonate and DMAPA (INCI: Polyquaternium43).

Understandably the composition according to the invention can include conventional cosmetic additive ingredients, such as perfume oils, in an amount of preferably from 0.01 to 5 percent by weight; propellants, such as ethylene glycol distearate, styrene/PVP copolymers or polystyrenes, in an amount of preferably from 0.01 to 5 percent by weight; moisturizing agents, dyestuffs, light-protecting agents, antioxidants, luster-producing agents and preservatives, in an amount of preferably from 0.01 to 10 percent by weight.

The composition according to the invention produces an improvement in the shapability, a long-lasting luster and soft feel to the hair and behaves like an oil without containing any oil as its principal ingredient in the classical sense.

Furthermore the production of a very beautiful moisturizing effect, also known as the wet-look, is possible with the composition according to the invention.

An especially suitable preferred embodiment of the composition according to the invention contains (A) at least one polyethylene glycol glyceryl fatty acid ester with at least 30 ethylene glycol units, (B) an ethoxylated hydrogenated castor oil, and (C) at least one thickener selected from the group consisting of ethyl cellulose, cross-linked polyacrylic acids or their mixtures.

The following examples serve to illustrate claimed in the claims appended hereinbelow without limiting their scope.

EXAMPLES

Example 1
Hair Treatment Composition for Gentle Hair Shaping 0.75 g hydrogenated polyethylene glycol (200)-glyceryl palmitate
0.25 g polyethylene glycol(7)-glyceryl cocoate
9.0 g hydrogenated castor oil, ethoxylated with 40 mol ethylene oxide
0.50 g hydroxyethyl cellulose
0.01 g aminomethylpropanol
to 100 g water

Example 2
Hair Treatment Composition for Gentle Hair Shaping 5.25 g hydrogenated polyethylene glycol (200)-glyceryl tallowate
1.75 g polyethylene glycol(7)-glyceryl cocoate
1.50 g Laureth-4
0.50 g Carbomer K neutralized with aminomethylpropanol
to 100 g water

Example 3
Hair Treatment Composition with Care Effect 0.7 g hydrogenated polyethylene glycol (200)-glyceryl palmitate
9.0 g hydrogenated castor oil, ethoxylated with 35 mol ethylene oxide
3.0 g cetyltrimethylammonium chloride
0.5 g cellulose gum
to 100 g water

Example 4
Hair Treatment Composition with Care Effect 5.25 g hydrogenated polyethylene glycol (200)-glyceryl palmitate
1.75 g polyethylene glycol(7)-glyceryl cocoate
0.9 g hydrogenated castor oil, ethoxylated with 35 mol ethylene oxide
0.30 g glucose decyl ether
1.0 g amodimethicone
0.5 g guar gum
to 100 g water

Example 5
Hair Treatment Composition with Strong Luster and Wet Effect 7.0 polyethylene glycol (30)-glyceryl cocoate
10.0 g polyethylene glycol
3.0 g Laureth-4
0.6 hydroxyethyl cellulose
to 100 g water

Example 6
Hair Treatment Composition with Quick Drying Effect 7.0 g polyethylene glycol (80)-glyceryl cocoate
3.0 g Oleth-10
20.0 g ethanol
0.7 g Carbopol ETD 2020 neutralized with aminomethylpropanol
to 100 g water

Example 7
Hair Treatment Composition with Quick Drying Effect 7.0 g polyethylene glycol (80)-glyceryl tallowate
9.0 g hydrogenated castoer oil, ethoxylate with 40 mol ethylene oxide
20.0 g ethanol
0.3 g xanthan gum
to 100 g water

Example 8
Hair Treatment Composition with Fixing Effect 7.0 g hydrogenated polyethylene glycol (200)-glyceryl palmitate
0.2 g polyoxyethylene (120)-methyl glucose dioleate
3.0 g Polysorbate 40
4.0 g polyvinyl pyrrolidone (Luvsikol® K60, BASF)
0.5 g Carbopol 980 neutralized with AMP
to 100 g water

Example 9
Hair Treatment Composition with Fixing Effect 5.25 g hydrogenated polyethylene glycol (200)-glyceryl palmitate
1.75 g polyethylene glycol (7)-gylceryl cocoate
3.0 g Polysorbate 20
2.0 g vinyl acetate/crotonate copolymer (Luviset® CA-66, BASF) neutralized with AMP
0.5 g Carbopol 980 neutralized with AMP
to 100 g water

Example 10
Hair Treatment Composition with Fixing Effect 7.0 g polyethylene glycol (80)-glyceryl tallowate
3.0 g polyethylene glycol (400) monooleate
4.0 g vinyl pyrrolidoneldimethylaminoethyl methacrylate methosulfate copolymer, 20% in water (Gafquat® 755 N, ISP)
0.5 g methylhydroxyethyl cellulose (Tylose®)
to 100 g water

Example 11
Hair Treatment Composition with Fixing Effect 5.25 g hydrogenated polyethylene glycol (200)-glyceryl tallowate
1.75 g polyethylene glycol(7)-glyceryl cocoate
9.0 g hydrogenated castor oil, ethoxylated with 40 mol ethylene oxide 1.0 g octylacrylamide/acrylate/
butylaminoethylmethacrylate copolymer
(Amphomer®, National Starch) neutralized with AMP 0.2 g Carbopol 980 neutralized with AMP 0.3 g hydroxyethyl cellulose (Natrosol® HHR)

to 100 g water

Example 12

Hair Treatment Composition with Fixing Effect 5.25 g hydrogenated polyethylene glycol (200)-glyceryl tallowate 1.75 g polyethylene glycol(7)-glyceryl cocoate 3.0 g Laureth-23

0.6 g chitosan 0.5 g xanthan gum to 100 g water

The disclosure in German Patent Application 199 24 705.6-43 of May 28, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a hair styling oil, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair treatment composition having the rheological properties of an oil but containing non-hydrophobic ingredients, said hair treatment composition having a viscosity of from 200 to 4000 mm²/s at 25° C. and comprising:

at least one fatty acid glyceride polyalkylene glycol ether or at least one fatty acid partial glyceride polyalkylene glycol ether with at least 30 alkylene glycol units respectively;

at least one surfactant different from said at least one fatty acid glyceride polyalkylene glycol ether and at least one fatty acid partial glyceride polyalkylene glycol ether with at least 30 alkylene glycol units; and at least one thickener;

wherein the hair treatment composition is free of ingredients that cause foaming of the composition prior to or during application to hair.

2. The hair treatment composition as defined in claim 1, wherein said at least one fatty acid glyceride polyalkylene glycol ether or said at least one fatty acid partial glyceride polyalkylene glycol ether with at least 30 alkylene glycol units respectively is a compound of formula (I):

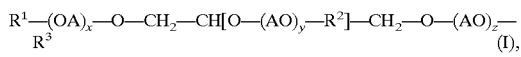

wherein $R^1$, $R^2$ and $R^3$ are each, independently of each other, hydrogen or a saturated or unsaturated, branched or non-branched $C_6$- to $C_{22}$-acyl group, with the proviso that at least one of the $R^1$, $R^2$ and $R^3$ is one of the saturated or unsaturated, branched or non-branched $C_6$- to $C_{22}$-acyl groups; A is an alkylene group with two or three carbon atoms; x, y and z are each from 0 to 1000, and the sum x+y+z is 30 to 1000.

3. The hair treatment composition as defined in claim 2, wherein said $R^1$ is said hydrogen, said $R^2$ is said H or said $C_6$- to $C_{22}$-acyl group and said $R^3$ is said $C_6$- to $C_{22}$-acyl group, said A is a ethylene group and said x and said y are both 0.

4. The hair treatment composition as defined in claim 1, wherein said at least one fatty acid glyceride polyalkylene glycol ether or said at least one fatty acid partial glyceride polyalkylene glycol ether is hydrogenated glyceryl palmitate with about 200 polyethylene glycol units.

5. The hair treatment composition as defined in claim 1, containing from 0.1 to 30 percent by weight of said at least one fatty acid glyceride polyalkylene glycol ether or said at least one fatty acid partial glyceride polyalkylene glycol ether.

6. The hair treatment composition as defined in claim 1, wherein said at least one surfactant different from said at least one fatty acid glyceride polyalkylene glycol ether and at least one fatty acid partial glyceride polyalkylene glycol ether is a nonionic surface-active compound.

7. The hair treatment composition as defined in claim 6, wherein said nonionic surface-active compound is selected from the group consisting of ethoxylated fatty acids, ethoxylated fatty alcohols, glyceride alkyoxylates, fatty acid glyceride polyalkylene glycol ethers with less than 30 alkylene glycol units, fatty acid partial glyceride polyalkylene glycol ethers with less than 30 alkylene glycol units, polyglycol amides, ethoxylated fatty acid polyol esters, non-ethoxylated fatty acid polyol esters and alkyl polyglycosides.

8. The hair treatment composition as defined in claim 1, containing from 0.1 to 30 percent by weight of said at least one surfactant different from said at least one surfactant different from said at least one fatty acid glyceride polyalkylene glycol ether and at least one fatty acid partial glyceride polyalkylene glycol ether.

9. The hair treatment composition as defined in claim 1, wherein said at least one thickener is selected from the group consisting of nonionic polymers and anionic polymers.

10. The hair treatment composition as defined in claim 1, containing from 0.05 to 3 percent by weight of said at least one thickener.

11. The hair treatment composition as defined in claim 1, further comprising a solvent containing at least one member selected from the group consisting of water and lower alcohols containing from 1 to 4 carbon atoms.

12. The hair treatment composition as defined in claim 1, further comprising at least one film-forming, hair-fixing polymer.

13. The hair treatment composition as defined in claim 12, containing from 0.01 to 10 percent by weight of said at least one film-forming hair-fixing polymer.

14. A hair treatment composition having the rheological properties of an oil but containing non-hydrophobic ingredients, said hair treatment composition having a viscosity of from 200 to 4000 mm²/s at 25° C. and comprising:

at least one fatty acid glyceride polyalkylene glycol ether or at least one fatty acid partial glyceride polyalkylene glycol ether with at least 70 alkylene glycol units respectively;

at least one surfactant different from said at least one fatty acid glyceride polyalkylene glycol ether and at least one fatty acid partial glyceride polyalkylene glycol ether with at least 70 alkylene glycol units; and at least one thickener;

wherein the hair treatment composition is free of ingredients that cause foaming of the composition prior to or during application to hair.

* * * * *